United States Patent [19]

Miller

[11] Patent Number: 5,311,861
[45] Date of Patent: May 17, 1994

[54] BREATHING APPARATUS

[76] Inventor: Donald M. Miller, 4 Weltevreden, Pinelands, 7405, South Africa

[21] Appl. No.: 961,453

[22] Filed: Oct. 15, 1992

[30] Foreign Application Priority Data

Aug. 24, 1992 [ZA] South Africa .................. 92/6365

[51] Int. Cl.⁵ .......................................... A61M 16/00
[52] U.S. Cl. .......................... 128/201.13; 128/204.28; 128/205.14; 128/909; 128/912; 128/204.26
[58] Field of Search .................. 128/201.13, 204.18, 128/204.28, 205.13, 205.14, 909, 911, 912, 203.12, 204.26, 200.24; 165/119

[56] References Cited

U.S. PATENT DOCUMENTS

| | | | |
|---|---|---|---|
| 3,814,091 | 6/1974 | Henkin | 128/909 X |
| 3,901,230 | 8/1975 | Henkin | 128/909 X |
| 3,923,053 | 12/1975 | Jansson | 128/205.13 X |
| 3,945,378 | 3/1976 | Paluch | 128/201.13 |
| 4,821,712 | 4/1989 | Gossett | 128/205.15 |

FOREIGN PATENT DOCUMENTS 334686  6/1936  Italy ......................... 128/205.13

Primary Examiner—Edgar S. Burr
Assistant Examiner—Eric P. Raciti
Attorney, Agent, or Firm—Ladas & Parry

[57] ABSTRACT

The breathing apparatus disclosed includes a first connector structure which provides ports for connection to a supply of fresh breathing gases, to an afferent gas tube and to an afferent gas bag. The first connector structure also provides a port to which a ventilator can be connected, a port to which an efferent gas tube can be connected, and a connection to an efferent gas bag. The afferent gas tube is of larger diameter than the efferent gas tube. The apparatus further includes a second connector construction to which said tubes are connected and which has a port for connection to the patient. The second connector structure causes preferential flow between the patient port and the afferent gas tube port.

9 Claims, 3 Drawing Sheets 5,311,861

BREATHING APPARATUS

FIELD OF THE INVENTION

This invention relates to breathing apparatus.

BACKGROUND TO THE INVENTION

In my earlier U.S. Pat. No. 4281652 I disclosed anaesthesia breathing apparatus based on a preferential flow directing means resulting in a valveless Mapleson A system convertible to a Mapleson D or E, thereby combining the advantages of all the systems with the smallest fresh gas flow requirements.

OBJECTS OF THE PRESENT INVENTION

The main object of the present invention is the provision of a breathing apparatus which is more efficient in its utilization of breathing gases than known systems.

Another object of the present invention is to provide a disposable breathing apparatus thereby reducing the risk of cross infection.

Yet another object of the present invention is to provide breathing apparatus from which the dead space has been almost entirely eliminated.

A still further object of the present invention is to provide breathing apparatus with improved heat and moisture exchange.

An additional object is to provide breathing apparatus which is entirely valveless and hence simple to use.

BRIEF DESCRIPTION OF THE INVENTION

According to one aspect of the present invention there is provided breathing apparatus comprising a first connector structure having a first port for connection to a supply of fresh breathing gas, a second port, an afferent gas tube having one and other ends with said one end thereof connected to said second port, a third port, an efferent gas tube having one and other ends with said one end thereof connected to said third port, a first flow path within the first connector structure placing said first and second ports in communication with one another, a fourth port for connection to a ventilator, a squeeze bag or a scavenger, a second flow path within said first connector structure placing said third and fourth ports in communication with one another, a breathing bag construction comprising a first afferent gas compartment and a second efferent gas compartment separated by a diaphragm wall, said first connector structure being attached to said bag construction with said first flow path in communication with said afferent compartment and said third and fourth ports in communication with said efferent compartment, and a second connector structure having an afferent port, an efferent port and a patient port for connection to the patient, the other end of said afferent tube being connected to said afferent port of the second connector structure and the other end of said efferent tube being connected to said afferent port of the second connector structure, the second connector structure including flow control means for causing preferential flow between said afferent port and said patient port, the volume of the afferent gas tube exceeding said volume of the efferent gas tube.

Said second connector structure preferably comprises an outer casing having first and second ends, said first end being a closed end and the second end being an open end, an inner pipe having a first portion which lies partly within the outer casing and a second portion which lies outside said outer casing, there being an annular space between the outer casing and said first portion of the inner pipe, said inner pipe protruding from said outer casing through the first end thereof, the end of said pipe remote from said casing constituting said afferent port, said efferent port being in the wall of said outer casing and communicating with said annular space, said inner pipe terminating between said efferent port and said second end of the outer casing, which second end constitutes the patient port. In this form, for ease of gas tube connection, said second portion of said pipe can have a right angled bend therein to provide a tube connection pipe which is at right angles to said first portion of the inner pipe, said efferent port being constituted by a tube connection pipe protruding from said outer casing, the two connection pipes being parallel to one another and on the same side of said casing as one another.

In the preferred form said breathing bag construction comprises two bags of sheet synthetic plastics material, the bag constituting the efferent compartment being entirely within the bag constituting the afferent compartment.

Said bags can have registering inlet openings and said first connector structure can comprise first and second co-axial tubes, the first tube being the inner of the two tubes and protruding from the second tube, passing through the inlet opening of the afferent bag and being connected to the inlet opening of the efferent bag, and the second tube being connected to the inlet opening of the afferent bag.

To prevent separation of said second tube and the afferent bag said second tube can include a snap-connector. Said first tube can include means for holding said inlets spaced apart.

Said first connector structure can also include flow directing means for causing gases flowing into the first connector structure through said fourth port to be preferentially directed away from said third port and into said efferent compartment.

According to a further aspect of the present invention there is provided a connector structure for breathing apparatus, the connector structure comprising an outer casing having first and second ends, said first end being an open end and said second end being a closed end, an inner pipe which lies partly within the outer casing and has a first portion which is within the outer casing and a second portion which lies outside said outer casing, there being a flow restricting annular space between said first portion and said casing and said inner pipe projecting from said outer casing through said first end thereof, said second portion providing a port for connection to an afferent gas tube, a port in the wall of said casing for connection to an efferent gas tube, the latter port communicating with said annular space between the outer casing and said first portion of the inner pipe, said second portion of said inner pipe terminating between said port of the outer casing and said second end of the outer casing.

According to a still further aspect of the present invention there is provided a breathing bag construction for breathing apparatus, the construction comprising a first bag having an inlet and a second bag having an inlet the second bag being entirely within the first bag and said inlets registering with one another, said bags being of sheet synthetic plastics material which has minimal ability to stretch when the bags are inflated.

According to another aspect of the present invention there is provided breathing apparatus including a breathing bag construction comprising a first afferent gas compartment and a second efferent gas compartment, a diaphragm wall between said compartments, an afferent gas tube, an efferent gas tube, the afferent gas tube being of larger diameter than said efferent gas tube, a first connector structure having an inlet for fresh breathing gases, a connection to said afferent compartment, a connection to said afferent gas tube, a first flow path placing said inlet and said connections in communication with one another, a connection to which a ventilator can be attached, a connection to said efferent gas compartment, a connection to said efferent gas tube, and a second flow path placing the ventilator connection, the connection to the efferent gas compartment and the connection to the efferent gas tube in communication with one another, and a second connector structure providing a first port to which the afferent tube is connected, a second port to which the efferent tube is connected, and a third port for connection to a patient, the second connector structure including flow control means for causing preferential flow between said first and third ports.

BRIEF DESCRIPTION OF THE DRAWINGS

For a better understanding of the present invention, and to show how the same may be carried into effect, reference will now be made, by way of example, to the accompanying drawings in which.

DETAILED DESCRIPTION OF THE DRAWINGS

Figure 1:
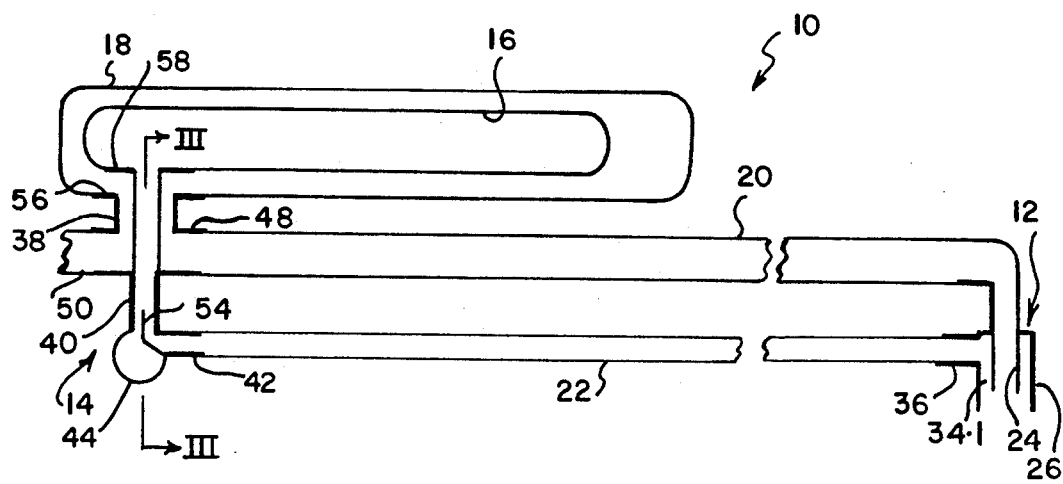
FIG. 1 is a diagrammatic representation of respiratory breathing apparatus in accordance with the present invention.

Referring firstly to FIG. 1, the respiratory breathing apparatus which is diagrammatically illustrated is generally designated 10 and comprises two connector structures 12 and 14, an inner reservoir bag 16, an outer reservoir bag 18, a larger diameter bore afferent gas tube 20 and a smaller diameter bore efferent gas tube 22.

Figure 2:
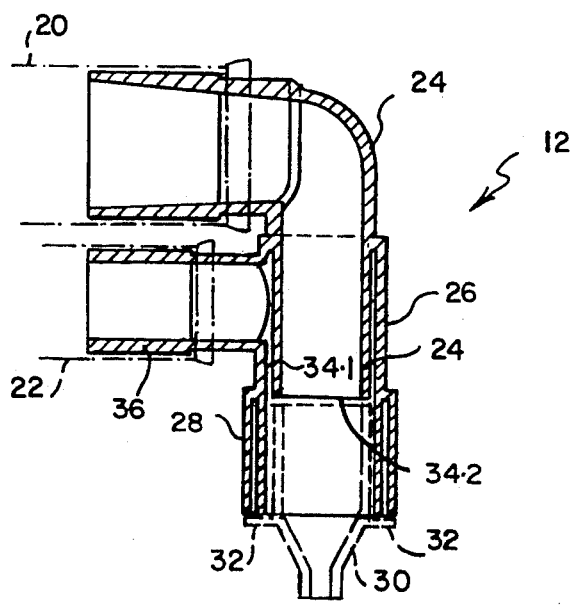
FIG. 2 is a section illustrating the connector structure which connects the efferent and afferent tubes to the endotracheal tube, laryngeal mask tube or face mask.

The connector structure 12 (see FIG. 2) comprises a pipe 24 which has a right angled bend in it and which changes diameter at the bend. This arrangement is designed to avoid as far as possible introducing turbulence into the gas flow. The afferent tube 20 is secured to the free end of the larger diameter limb of the pipe 24. The connector structure 12 further includes an outer cylindrical casing 26 which is of larger diameter than the pipe 24. The upper end of the casing 26, from which upper end the pipe 24 protrudes, is closed off around pipe 24.

The other end of the casing 26 forms a socket 28 into which an endotracheal tube connector, a laryngeal mask tube connector or a face mask connector can be inserted. The connector, which is designated 30, is shown in dotted lines and includes two wings 32 which, as the connector 30 reaches its fully inserted position, engage the lower end of the casing 26. This limits insertion of the connector 30 into the connector structure 12, the inner end of the connector 30 being adjacent, but not touching, that end of the pipe 24 which is within the casing 26. This leaves a gap between the connector 30 and the end of the pipe 24. The outside diameter of the pipe 24 is smaller than the inside diameter of the casing 26 whereby there is a annular space 34.1 between them.

A pipe 36 protrudes laterally from the casing 26 and parallel to the larger diameter limb of the pipe 24. The smaller diameter bore efferent gas tube 22 is attached to the pipe 36.

The port constituted by the interior of the pipe 36 communicates with the annular space 34.1 and this space in turn communicates with the interior of the flow path constituted by the aligned pipe 24 and connector 30 by way of the gap 34.2 between the end of the pipe 24 and the inner end of the connector 30. The dimensions are such that the connector 30 can never be inserted far enough to reduce the flow area of the gap 34.2 to less than the flow area of the annular space 34.1.

Figure 3:
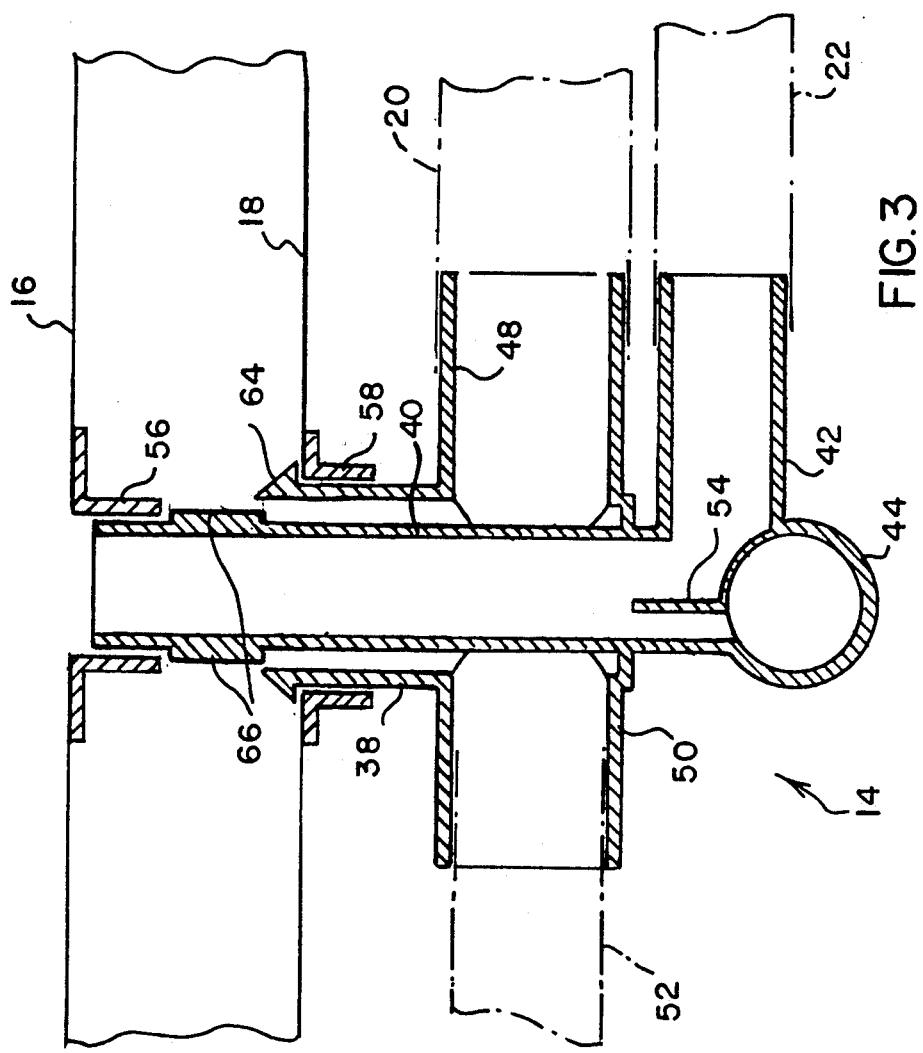
FIG. 3 is a section on the line III—III of FIG. 1 and illustrates a further connector structure.

The connector structure 14 (see FIG. 3) comprises an outer tube 38 and an inner tube 40 which is co-axial with the tube 38. The tube 40 protrudes in both directions from the tube 38. One protruding portion passes through the wall of the outer bag 18 and communicates with the interior of the inner bag 16. The other protruding end of the inner tube 40 has two sleeves 42 and 44 protruding therefrom, the sleeves 42 and 44 being at right angles to one another (see particularly FIG. 5). The efferent tube 22 is connected to the sleeve 42. The interior of the sleeve 42 is connected to the interior of the tube 40. The sleeve 44 is open at both ends as will be described in more detail hereinafter with reference to FIG. 5.

Two short co-axial sleeves 48 and 50 protrude in opposite directions from the outer tube 38. The afferent gas tube 20 is connected to the short sleeve 48 and the sleeve 50 is fitted over the fresh gas outlet tube 52 from an anaesthetic machine or other fresh gas source.

A flow directing vane 54 is provided within the tube 40 and is arranged so that when, during operation of the apparatus, gas flows in from the ventilation means connected to the sleeve 44, it is directed along the inner tube 40 and into the inner bag 16 rather than flowing directly into the efferent tube 22.

The tubes 40 and 38 are respectively pushed into flanges 56 and 58 which are themselves secured to the walls of the bags 16 and 18 respectively. The flanges 56 and 58 are diagrammatically shown in FIG. 3 and are shown in more detail in FIG. 4

Each bag 16 and 18 comprises two sheets of synthetic plastics material. The edges of the sheets constituting the bag 16 are welded together at 60 (see FIG. 4) and the edges of the two sheets constituting the bag 18 are welded together at 62. It will be noted that the bag 16 is entirely enclosed by the bag 18.

The flanges 56 and 58 are welded to the sheet material which constitutes the bags 16 and 18 in register with inlet/outlet openings cut in the sheet material. The openings of the bags are in register with one another.

The end of the outer tube 38 which pushes into the flange 58 is formed at its free end with a snap connector 64 which, once pushed through the flange 58, prevents the tube 38 and bag 18 thereafter being separated. It will be seen from FIG. 3 that the connector 64 includes a taper to facilitate its insertion into the flange 58. The connector 64 also includes a rear annular face which, if an attempt is made to separate the flange 58 and tube 38, bears on the inner end of the flange 58 preventing such removal.

Figure 4:
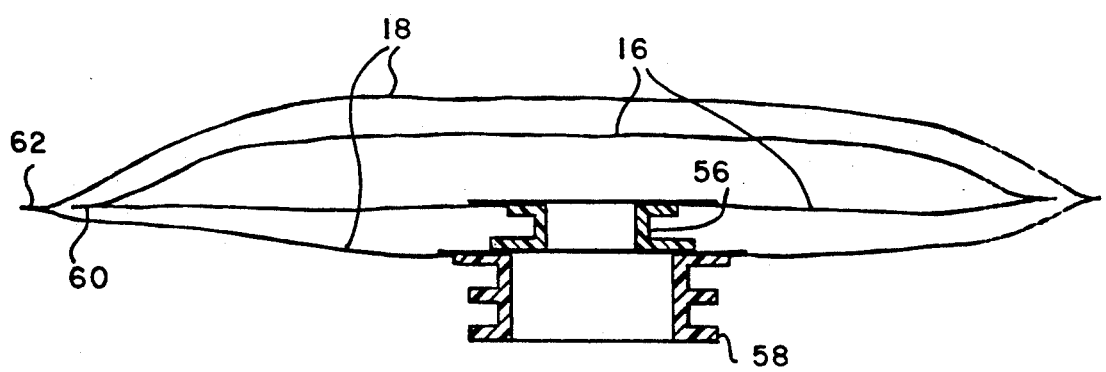
FIG. 4 illustrates two breathing bags prior to attachment to the connector structure of FIG. 3.

Two diametrically opposed ribs 66 (or a circumferentially spaced array of ribs) are provided on the outer face of the inner tube 40. These ribs terminate short of that end of the tube 40 which is inserted into the flange 56. By contacting the end of the flange 56 during insertion of the tube 40 into the flanges 56, the ribs 66 limit insertion. This prevents the tube 40 being pushed so far into the bag 16 that the annular opening through which the tube 38 communicates with the bag 18 is closed-off. Thus, whilst the flanges 56 and 58 can touch before the bags 16 and 18 are attached to the connector structure 14 (as shown in FIG. 4), they are held apart after connection so that the vital passages are maintained open.

Figure 5:
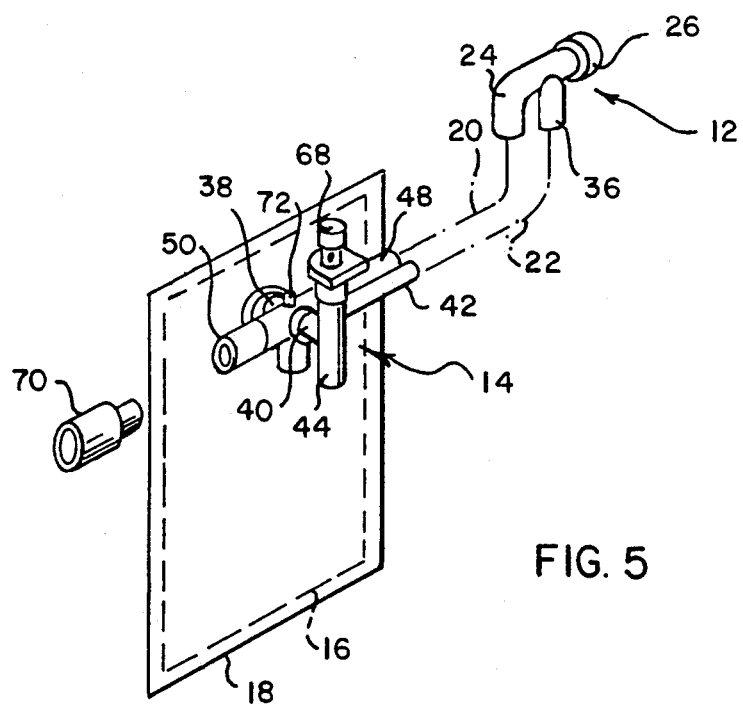
FIG. 5 is a pictorial view of the breathing apparatus.

Turning now to FIG. 5, the bags 16,18 are shown in the vertical position with the connector structure 14 adjacent one vertical side face of the bag 18. The sleeve 50 and the side-by-side sleeves 42 and 48 lie horizontally with the sleeve 44 vertical. The lower end of the sleeve 44 is intended for attachment to a ventilator or squeeze bag (neither of which has been illustrated). At the upper end of the sleeve 44 there is a valve 68 which provides controlled leakage from the efferent side of the breathing apparatus. The valve 68 can leak directly to atmosphere or be connected to a scavenging apparatus (not shown).

The tubes 20 and 22 (which are preferably standard 22 mm and 15 mm corrugated hoses) run from the connector structure 12 to the connector structure 14 which, in FIG. 5, is illustrated with the efferent and afferent tube connections directed downwardly and the port which is connected to the patient directed horizontally.

If desired an endotracheal cuff pressure regulator designated 70 can be connected between the fresh gas supply and the sleeve 50. Normally closed port 72 can be used as a connection for a pressure gauge.

The apparatus can be used for both spontaneous ventilation and controlled ventilation and is designed to eliminate alveolar gases whilst retaining tracheal gases, that is, largely unused gases.

During spontaneous ventilation, the sleeve 44 can be connected to non-functioning ventilation means but the valve 68 must be open and communicate with a scavenging means (not shown) or to atmosphere. If a scavenging means is connected to the sleeve 44 via the valve 68 it maintains a slightly negative pressure in the efferent part of the system. The valve 68 is normally fully open unless there is a tendency for the bag 18 to collapse in which event the valve 68 can be partly closed. It is also partly closed when a squeeze bag is used. Fresh gases pass continuously into the afferent gas part of the apparatus via the port constituted by the sleeve 50, entering the outer tube 38, the afferent gas tube 20 and the outer reservoir bag 18. Gas pressure causes the outer reservoir bag 18 to distend and the inner reservoir bag 16 to collapse. During the inspiratory phase of the breathing cycle, fresh gases are drawn by the patient from the bag 18 into the afferent tube 20, and then flow along the pipe 24 into the connector 30 and thence to an endotracheal tube, to a laryngeal mask tube or to a face mask. During this phase of the breathing cycle, the outer bag 18 collapses and inhibits any tendency of the inner bag 16 to expand. Flow resistance in the afferent part of the apparatus (which part includes the tube 38, bag 18, tube 20 and pipe 24) is lower than the flow resistance in the efferent part of the apparatus (which includes the annular space 34.1, the tube 22, and the tube 40). The result of this is that only a very small portion of previously exhaled gases which are in the efferent tube 22 enter the patient during inhalation.

During exhalation, gases being exhaled are directed initially into the afferent gas tube 20 because the connector 30 and pipe 24 are axially aligned and the only communication with the tube 22 is by way of the restricted annular space 34.1 between the pipe 24 and casing 26. This space acts as a flow restrictor. The bulk of the dead space gases, that is, the tracheal gases, enter the tube 20 followed by a small quantity of alveolar gases. The outer bag 18 expands and holds the inner bag 16 collapsed. Once the bag 18 is fully distended, the pressure within the afferent tube 20 increases and exhaled alveolar gases flow through said flow restricting annular space 34.1 into the tube 22. The exhaled gases flow to exhaust via the tube 22, the sleeve 42, the tube 40 and the sleeve 44.

It will be understood from this description that, during spontaneous ventilation, the inner bag 16 remains collapsed all of the time.

For forced ventilation the scavenging means (if present) can be left attached but the valve 68 is closed and a ventilator (if not already present) is connected to the sleeve 44. To force the patient to inhale, an increasing pressure is applied by the ventilator to the sleeve 44, and hence to the inner tube 40, the inner reservoir bag 16 and the efferent gas tube 22. As the inner reservoir bag 16 expands the volume of the outer bag 18 (which is filled mainly with fresh gases with possibly a small amount of tracheal gases) decreases and the pressure therein increases. The contents of the outer bag are thus forced along the tube 20 and eventually into the patient's lungs.

The vane 54 directs gases flowing into the inner tube 40 from the ventilator via the sleeve 44 towards the inner reservoir bag 16 and away from the efferent tube 22. The pressure within the efferent tube 22 does, of course, tend to rise with the rise in pressure in the entire system, but the differential pressures in the system greatly favour flow to the patient from the afferent side rather than from the efferent side.

The same pattern of gas elimination occurs regardless of whether the apparatus is being used for spontaneous ventilation or for controlled ventilation using a ventilator. The apparatus can also be used in the mode that is known as continuous positive airway pressure. This is a spontaneous breathing mode but one in which a ventilator maintains a continuous positive pressure in both the afferent and the efferent sides of the apparatus.

If a face mask is being used, the connector structure 12 can be fitted directly to the mask. The inner pipe 24 encourages streaming of incoming gas in the mask such that exhaust gases flow on the outside of the central stream causing the fresh gas delivery site to extend into the mask cavity resulting in a decrease in dead space within the mask.

The material used for the bags 16 and 18 must be incapable of stretching to any significant extent. Thus once a bag has fully distended it reaches a maximum volume and cannot thereafter increase in volume as a result of the material stretching.

I claim:

1. Breathing apparatus comprising a first connector structure having a first port for connection to a supply of fresh breathing gas, a second port, an afferent gas tube having one end and another end with said one end thereof connected to said second port, a third port, an efferent gas tube having one end and another end with said one end thereof connected to said third port, a first flow path within the first connector structure placing said first and second ports in communication with one another, a fourth port for connection to a ventilator, a squeeze bag or a scavenger, a second flow path within said first connector structure placing said third and fourth ports in communication with one another, a breathing bag construction comprising a first afferent gas compartment and a second efferent gas compartment separated by a diaphragm wall, said first connector structure being attached to said bag construction with said first flow path in communication with said first afferent compartment and said third and fourth ports in communication with said second efferent compartment, and a second connector structure having an afferent port, an efferent port and a patient port for connection to the patient, the other end of said afferent tube being connected to said afferent port of the second connector structure and the other end of said efferent tube being connected to said efferent port of the second connector structure, the second connector structure including flow control means for causing preferential flow between said afferent port and said patient port, the volume of the afferent gas tube exceeding said volume of the efferent gas tube.

2. Breathing apparatus according to claim 1 in which said second connector structure comprises an outer casing having first and second ends, said first end being a closed end and the second end being an open end, an inner pipe having a first portion which lies partly within the outer casing and a second portion which lies outside said outer casing, there being an annular space between the outer casing and said first portion of the inner pipe, said inner pipe protruding from said outer casing through the first end thereof, the end of said pipe remote from said casing constituting said afferent port, said efferent port being in the wall of said outer casing and communicating with said annular space, said inner pipe terminating between said efferent port and said second end of the outer casing, which second end constitutes the patient port.

3. Breathing apparatus according to claim 2, in which said second portion of said pipe has a right angled bend therein to provide a tube connection pipe which is at right angles to said first portion of the inner pipe, said efferent port being constituted by a tube connection pipe protruding from said outer casing, the two connection pipes being parallel to one another and on the same side of said casing as one another.

4. Breathing apparatus according to claim 1, in which said breathing bag construction comprises first and second bags of sheet synthetic plastics material, said first bag constituting the second efferent compartment and being entirely within the second bag which constitutes the first afferent compartment, each of said bags having a respective inlet.

5. Breathing apparatus according to claim 4 in which said bags have registering inlet openings and said first connector structure comprises first and second co-axial tubes, the first tube being the inner of the two tubes and protruding from the second tube, passing through the inlet opening of the afferent bag and being connected to the inlet opening of the efferent bag, and the second tube being connected to the inlet opening of the afferent bag.

6. Breathing apparatus according to claim 5, in which said second tube includes a snap-connector for preventing separation of said second tube and the afferent bag.

7. Breathing apparatus according to claim 5, in which said first tube includes means for holding said bag inlets spaced apart.

8. Breathing apparatus according to claim 1, in which said first connector structure includes flow directing means for causing gases flowing into the first connector structure through said fourth port to be preferentially 9. Breathing apparatus including a breathing bag construction comprising a first afferent gas compartment and a second efferent gas compartment, a diaphragm wall between said compartments, an afferent gas tube, an efferent gas tube, the afferent gas tube being of larger diameter than said efferent gas tube, a first connector structure having an inlet for fresh breathing gases, a connection to said first afferent compartment, a connection to said afferent gas tube, a first flow path placing said inlet and said connections in communication with one another, a connection to which a ventilator can be attached, a connection to said second efferent gas compartment, a connection to said efferent gas tube, and a second flow path placing the ventilator connection, the connection to the efferent gas compartment and the connection to the efferent gas tube in communication with one another, and a second connector structure providing a first port to which the afferent tube is connected, a second port to which the efferent tube is connected, and a third port for connection to a patient, the second connector structure including flow control means for causing preferential flow between said first and third ports.

* * * * *